(12) United States Patent
Stewart et al.

(10) Patent No.: US 9,242,919 B2
(45) Date of Patent: Jan. 26, 2016

(54) PROCESS TO PREPARE OLEFINS FROM ALIPHATIC ALCOHOLS

(75) Inventors: Mark William Stewart, Pearland, TX (US); Howard W. Clark, Lake Jackson, TX (US); Duncan Paul Coffey, Lake Jackson, TX (US); Lin Luo, Sugar Land, TX (US); Albert E. Schweizer, Jr., Port St. Lucie, FL (US)

(73) Assignee: Dow Global Technologies LLC, Midland, MI (US)

( * ) Notice: Subject to any disclaimer, the term of this patent is extended or adjusted under 35 U.S.C. 154(b) by 246 days.

(21) Appl. No.: 13/320,931

(22) PCT Filed: Jun. 28, 2010

(86) PCT No.: PCT/US2010/040151
§ 371 (c)(1),
(2), (4) Date: Nov. 17, 2011

(87) PCT Pub. No.: WO2011/002699
PCT Pub. Date: Jan. 6, 2011

(65) Prior Publication Data
US 2012/0101320 A1    Apr. 26, 2012

Related U.S. Application Data

(60) Provisional application No. 61/222,174, filed on Jul. 1, 2009.

(51) Int. Cl.
*C07C 1/24*    (2006.01)
*C07C 41/09*    (2006.01)

(52) U.S. Cl.
CPC . *C07C 41/09* (2013.01); *C07C 1/24* (2013.01); *C07C 2521/04* (2013.01); *C07C 2521/06* (2013.01); *C07C 2521/08* (2013.01); *C07C 2521/12* (2013.01); *C07C 2523/28* (2013.01); *C07C 2523/30* (2013.01); *C07C 2527/167* (2013.01)

(58) Field of Classification Search
CPC .......................................................... C07C 1/20
USPC .................................................. 585/638–642
See application file for complete search history.

(56) References Cited

U.S. PATENT DOCUMENTS

| | | |
|---|---|---|
| 4,134,926 A | 1/1979 | Tsao et al. |
| 4,232,179 A | 11/1980 | Valladares Barrocas et al. |
| 4,396,789 A | 8/1983 | Barrocas et al. |
| 8,119,748 B2 | 2/2012 | Boone et al. |

FOREIGN PATENT DOCUMENTS

JP    3123739 A    5/1991

OTHER PUBLICATIONS

Barnard, J.A., Hughes, H.W.D., "The Pyrolysis of Ethanol," Transactions of the Faraday Society, 1960, 56, 55-63.
Cesar, M.A.N., "Chemicals from Ethanol," Process Economics Program (PEP), SRI Consulting, 2007, 235, 1-39.
Kochar, "Ethylene from Ethanol", from CEP, Jun. 1981.
Scheeline, H.W., Itoh, R., "Ethylene from Ethanol," Process Economics Program (PEP), SRI International, 1980, 79-3-4.
PCT/US2010/040151, International Search Report and Written Opinion.
PCT/US2010/040151, International Preliminary Report on Patentability.

*Primary Examiner* — In Suk Bullock
*Assistant Examiner* — Sharon Pregler

(57) ABSTRACT

A process to prepare an olefin from its corresponding alcohol is improved by reacting, under reaction conditions including a first temperature, an aliphatic alcohol and, optionally, diluent water, to form a reaction product including at least a dialkyl ether. The product is then reacted again, under higher temperature to complete the dehydration of the dialkyl ether to the desired olefin. This process is particularly suitable to prepare ethene from ethyl alcohol. The stepped temperature scheme serves to reduce the formation of byproduct aldehydes, which in turn reduces coke formation, fouling, and the need to handle large amounts of water, thereby lowering energy and capital costs.

10 Claims, No Drawings

PROCESS TO PREPARE OLEFINS FROM ALIPHATIC ALCOHOLS

BACKGROUND OF THE INVENTION

1. Field of the Invention

The invention relates to the field of production of olefins from alcohols. More particularly, it relates to the field of producing olefins by way of dehydrating alcohols in reactors under either adiabatic or isothermal conditions.

2. Background of the Art

Ethene is an important raw material in the world today and is known to be useful as a raw or starting material to prepare products as wide-ranging as packaging, detergents, chemical weapons agents, and anesthetics. It is also used as a welding gas and fruit ripening agent. It is particularly important in the field of plastics production, and a majority of the global ethene production goes toward this purpose. Because of its carbon-carbon double bond it is highly reactive, enabling a wide variety of useful polymerization products.

Methods to prepare ethene have been known since the late $18^{th}$ century, when it was discovered that it could be made by passing ethyl alcohol over a heated catalyst. This method was common for decades until it was discovered in the 1950's that it could more economically be obtained via steam cracking of naphtha, which converted longer-chain hydrocarbons to shorter-chain hydrocarbons and introduced unsaturation. This is a laborious and very energy-intensive process, which was propagated primarily during a time period when petroleum reserves seemed endless and relatively inexpensive. At the present time, however, petroleum-based processes may be considered to be less desirable and, therefore, new and improved methods to produce ethene are being sought.

One method that has been described is the preparation of ethene by dehydration of ethyl alcohol, wherein ethyl alcohol vapor is passed over solid catalysts maintained at high temperature in multitubular, isothermal reactors. The isothermal conditions are maintained by circulating a heating fluid externally to the tubes, thereby indirectly heating the ethyl alcohol vapor. A problem with this method, however, is that such heating fluids necessarily exhibit a high boiling point and high thermal stability, and include certain organic liquids and low melting inorganic salts. Few organic liquids can be maintained at a temperature greater than 370° C. without degradation, while molten salts, which may be heated to 550° C., are likely to be solid at temperatures below 150° C. This change of state may result in highly problematic obstruction when plant equipment either fails or is shut down. Molten salts may cause equipment corrosion, while equipment materials that can withstand temperatures greater than 450° C. include only certain expensive steels. Furthermore, if molten salts and organic vapors come into direct contact, flammability and safety issues may arise. Finally, the multitubular reactors, which offer the increased heat exchange area needed for the highly exothermal dehydration reaction, represent significant initial capital outlays, yet enable only a limited throughput rate.

Another method is disclosed in U.S. Pat. No. 4,134,926 (1979). That method includes the catalytic dehydration of ethyl alcohol to ethene in a fluidized catalyst bed. The use of the fluidized bed, at reaction temperatures of at least 700° F. (370° C.), preferably at least 750° F. to 900° F. (that is, 400° C. to 482° C.), and a reaction time from 1 to 10 seconds, is described as increasing overall yields to greater than 99 percent.

Yet another approach to catalytically preparing ethene from ethyl alcohol is disclosed in U.S. Pat. No. 4,232,179 (1980). In that process an ethyl alcohol feed is introduced to the catalyst simultaneously with a "sensible" heat carrying fluid, which may be selected from, for example, a part of the effluent from the reactor used as a recycle stream; steam supplied by an external source; other adequate fluids for the process; or any combination thereof. Adiabatic reactors containing a fixed catalyst bed are used, singly, in parallel or in series, enabling catalyst exchange, maintenance, without detriment to process continuity. Because of the heat carrying fluid, multitubular reactors are not necessary and the heating fluid requires no independent circulation. Higher temperatures may therefore be used, which facilitate higher space velocities. The patent alleges reduction in by-product and coke deposition on the catalyst, but the relatively high amount of water reduces energy efficiency by requiring water separation and cleanup, which in turn requires additional processing equipment.

U.S. Pat. No. 4,396,789 (1983) discloses another process relating to dehydration of a low molecular weight alcohol to form ethene in fixed adiabatic reactors. This process uses a combination of a co-feed of ethyl alcohol and steam, at a temperature of 400° C. to 520° C. and a pressure from 20 to 40 atmospheres (that is, 2.03 to 4.05 megapascals (MPa)), in a plurality of adiabatic reactors containing a fixed bed catalyst, to accomplish the dehydration of the ethyl alcohol. Subsequent washing and purification steps are described as producing a higher purity ethene.

Despite efforts to discern an effective method of producing an olefin via dehydration of an alcohol, desirably under adiabatic conditions which become more economically favored as process scale increases, it has generally been found that large co-feeds of water or other heat-carrying diluents increase yields, but also undesirably increase costs, particularly those relating to energy and capital. At the same time, reducing water content requires more adiabatic reactors and increases byproduct production and fouling. Those skilled in the art therefore continue to search for adabatic processes whereby alcohols may be dehydrated to form olefins as conveniently and inexpensively as possible, and whereby problems arising from production of byproducts and coke deposition are minimized. The present invention provides such a process.

SUMMARY OF THE INVENTION

In one embodiment the invention provides a process to prepare an olefin, comprising reacting, under reaction conditions including a first temperature, an aliphatic alcohol and, optionally, diluent water, in a first adiabatic reactor of a reactor system including at least two adiabatic reactors, in the presence of a first dehydration catalyst, wherein the diluent water, if used, is in an amount of up to 50 percent by weight, based on the weight of the aliphatic alcohol, to form a first reaction product that includes at least a dialkyl ether and generated water; and, subsequently, reacting the first reaction product in a second adiabatic reactor under reaction conditions including a second temperature that is at least 10° C. higher than the first temperature, in the presence of a second dehydration catalyst, such that at least a portion of the dialkyl ether in the first reaction product is dehydrated to form an olefin; provided that the first dehydration catalyst and the second dehydration catalyst may be the same or different.

In another embodiment the invention provides a process to prepare ethene, comprising reacting, under reaction conditions including a first temperature, ethyl alcohol and, optionally, diluent water, in a first adiabatic reactor of a reactor system including at least two adiabatic reactors, in the presence of a first dehydration catalyst, wherein the diluent water, if used, is in an amount of up to 50 percent by weight, based on the weight of the ethyl alcohol, to form a first reaction product that includes at least diethyl ether and generated water; and, subsequently, reacting the first reaction product in a second adiabatic reactor under reaction conditions including a second temperature that is at least 10° C. higher than the first temperature, in the presence of a second dehydration catalyst, such that at least a portion of the diethyl ether in the first reaction product is dehydrated to form ethene; provided that the first dehydration catalyst and the second dehydration catalyst may be the same or different.

In still another embodiment the invention provides a process to prepare an olefin, comprising (a) heating an aliphatic alcohol and, optionally, diluent water, as reactants and feeding the reactants to a first adiabatic reactor of a reactor system including at least two adiabatic reactors, in the presence of a dehydration catalyst, wherein the diluent water, if present, is in an amount of up to 50 percent by weight, based on the weight of the aliphatic alcohol, under reaction conditions such that the aliphatic alcohol is at least partially dehydrated to form a first reaction product including at least generated water and a dialkyl ether; (b) exiting the first reaction product from the first adiabatic reactor, the first reaction product having an exit temperature; (c) heating the first reaction product to a second temperature at least 10° C. higher than its exit temperature, and feeding the first reaction product into a second adiabatic reactor; (d) subjecting the first reaction product in the second adiabatic reactor to reaction conditions, and in the presence of a dehydration catalyst, such that at least a portion of the dialkyl ether in the first reaction product is dehydrated to form an olefin; and (e) exiting the second reaction product from the second adiabatic reactor; provided that the first dehydration catalyst and the second dehydration catalyst may be the same or different.

DETAILED DESCRIPTION OF THE EMBODIMENTS

The invention enables those skilled in the art to prepare ethene and other lower-order olefins from their correspondingly-ordered aliphatic alcohols in the presence of conventional and other dehydration catalysts. This process may result in production of the desired olefin while reducing capital and energy expenditures, as well as byproduct formation and fouling.

The process is generally carried out using at least two reactors, under either adiabatic or isothermal conditions. Such reactors may be in series or in parallel series assemblies. This set-up enables the termination or start-up of the operation of one or more reactors, during normal processing of industrial units, without causing interruption of olefin production. While multitubular reactors may be employed in the invention, such are not necessary and, because of their relatively higher initial capital costs, are not preferred.

The reactors are desirably fitted with fixed catalyst beds, which ensure contact between the feed and the desired catalyst(s). Suitable catalysts for these beds include any known to those skilled in the art to be effective for the dehydration of the aliphatic alcohol to form the corresponding, that is, same carbon number, olefin. In certain non-limiting embodiments the catalyst may be selected from alumina; silica-alumina; silica; refractory metal oxides such as, for example, those of titanium, hafnium, zirconium, and tungsten; zeolites; phosphoric acids supported on carbon; calcium phosphates; calcium molybdates; and combinations thereof. In some embodiments preferred catalysts may include alumina and silica-alumina, which are readily available and relatively inexpensive.

The starting material employed in this process includes at least the selected aliphatic alcohol. In non-limiting example, where the desired final product is ethene, the selected aliphatic alcohol is ethyl alcohol. However, in additional and non-limiting embodiments, propanol and butanol, or a combination thereof, may alternatively be selected for conversion to their corresponding olefins. It may also be useful and, in some embodiments, desirable and/or convenient to include water or steam. The purpose of the water or steam is as a diluent, and as used herein, the term "diluent water" includes both liquid and vapor (that is, steam) forms. The water or steam may be used in any amount up to 50 percent by weight, based on the weight of the aliphatic alcohol. However, in general it is often desirable to reduce the amount of diluent water as much as possible, and therefore in certain alternative embodiments the amount of diluent water is up to 40 percent by weight, while in other embodiments it is up to 20 percent by weight; all based on the weight of the aliphatic alcohol. In still other embodiments the amount of water is at its azeotropic value with the aliphatic alcohol. For purposes herein the aliphatic alcohol, if used alone or together with diluent water, is referred to as the "feed" for the process.

Operation of the process of the invention requires contact between the feed and the catalyst bed, which contains the selected dehydration catalyst. A key to the invention is that at least two reactors are used, and that the conditions encountered by the feed for the initial reaction include a first temperature ranging from 200° C. to 450° C. and a first pressure ranging from 0.04 to 4 megapascals (MPa) absolute. It is important to note that in some embodiments it is most convenient to first heat the feed, in a furnace and with or without a prior evaporation step, to the desired temperature range as given herein, and then to subsequently introduce the heated feed into the first adiabatic reactor. The temperatures referenced herein therefore, for the sake of convenience, refer to the temperature of the reactant(s) as it/they are being fed into a reactor, which may be therefore also referred to as the "reactor inlet temperature." This avoids any misunderstanding that might result if the exothermic nature of the initial reaction were taken into account. Pressures and residence times, however, refer to those maintained within the reactor, and may be independently selected for each reactor to ensure the appropriate reaction, and degree of reaction, occurs.

Thus, in certain particular embodiments the "first temperature" may range from 250° C. to 425° C., while in other embodiments the first temperature may range from 350° C. to 425° C. Pressure in the first reactor may, in some embodiments, range from 0.1 to 2 MPa absolute; in other embodiments from 0.1 to 1.5 MPa absolute; and in still other embodiments from 0.1 to 1 MPa absolute. Times of contact between the feed and the catalyst, alternatively termed as a "residence time" within the first reactor and in contact with the catalyst, may range from 0.5 second to 1 minute, but in certain preferred embodiments may range from 0.5 second to 30 seconds, and in other preferred embodiments may range from 0.5 second to 10 seconds.

The purpose of the relatively low temperature range in the first reactor is to instigate dehydration of the aliphatic alcohol to primarily its corresponding dialkyl ether, which dehydration also serves to increase the water content of the first reaction product as compared with non-inventive processes that start with relatively larger amounts of water than the present process. For example, where ethyl alcohol is the feed, it is dehydrated in this first reaction to form primarily the diethyl ether and to generate water. It is a goal that only a relatively small amount of the ethyl alcohol will be likely to complete dehydration to form ethene in this first step.

The product of the conversion occurring in the first reactor is then flowed to at least one second reactor, still under adiabatic conditions. This product is termed the "first reaction product," and it is then further reacted to progress dehydration, of at least a portion of the dialkyl ether, to form the olefin. In some embodiments this progression may be to essentially complete such dehydration for maximum olefin production in just two steps, that is, two reactors, while in other embodiments the progression may be extended over more than two reactors, provided that the described steps occur in or at two contiguous reactors in the reactor train. Again, the temperature used for the second step (the "second temperature") may be interpreted as the "reactor inlet temperature," which avoids misunderstanding that might occur if the endothermic nature of this second reaction were taken into account. The second reaction desirably includes additional reaction conditions, including pressure and residence time, which continues the process by the dehydration of at least some of the dialkyl ether to form the corresponding olefin.

Regardless of whether a pre-heating of this type is carried out, and regardless of the actual temperature of the first reaction product upon exiting the first adiabatic reactor, the reaction that will occur primarily within the second adiabatic reactor is at a reactor inlet temperature, termed the "second temperature," that is specifically higher than that of the first reactor by at least 10° C. Accordingly, the temperature of the first reaction product during this second-stage reaction is desirably from 250° C. to 500° C.; more desirably from 275° C. to 475° C.; and most desirably from 400° C. to 450° C. Where there is a train of reactors following the first reactor, the temperatures in the reactors may each be based upon only the first reactor, or may continue to increase in a stepwise manner. In another embodiment, the two reactions defined by the invention may occur in reactors located in the middle or at the end of a reactor train. Whether two or many reactors are employed, it is in some embodiments desirable to increase the temperature from reactor to reactor by at least 10° C.; in other embodiments larger steps, such as increases of at least 20° C., may be desirable; and in still other embodiments increases of at least 50° C. may be desirable. Those skilled in the art will be able to discern optimal temperature gradients with, at most, routine experimentation. The effect of the temperature increase, whether over just two reactors or of multiple increases over many reactors, is that the amount of dialkyl ether may be progressively reduced as dehydration is carried to or toward completion, to form the final desired olefin, and the reduction in starting diluent water means that there is a minimum of corresponding aldehyde formed. Since such aldehyde is both itself an undesirable byproduct and also a contributor to coke formation, reduction in the amount of aldehyde formed is important to obtaining some of the benefits of the invention.

Other conditions for this second, and endothermic, reaction include pressures ranging from 0.04 to 4 MPa absolute, with the same selection of encompassed embodiments as for the first adiabatic reactor. It is generally understood, however, that due to flow across a furnace or heat exchanger to reheat the reactant(s), and where means are not employed to compress the flow between the reactors, the pressure in the second adiabatic reactor would generally be expected to be slightly less than the pressure in the first adiabatic reactor (and the third reactor's pressure will be slightly less than the second reactor's). Similarly, residence time in the second adiabatic reactor may vary over the same ranges, that is, from 0.5 second to 1 minute, with the same selection of encompassed embodiments as for the first adiabatic reactor. Nonetheless, pressures and residence times for the two reactors, as well as for any additional reactors employed in the inventive process, are selected independently of one another.

It will thus be seen by those skilled in the art that the inventive process essentially generates water and performs dehydration to an intermediate, the dialkyl ether, using the chemistry of the process under conditions that are generally milder than those conventionally used in the art, then completes the conversion of the dialkyl ether to the corresponding olefin by means of subsequent reactions under the higher second (or additional subsequent) temperature(s). The relatively milder conditions for the first reaction avoid or reduce later problems such as the need to handle high volumes of water, production of coke, and costs incurred in light of these problems. Thus, the invention offers a simple, economical, and surprising solution. While in many embodiments some amount of the desired olefin is co-created in the first reactor, because some portion of the dialkyl ether may complete dehydration therein, the yield of olefin may be significantly augmented in the second and, if employed, any subsequent reactors as the dehydration reaction runs to its completion.

It will be noted that, in order to further improve process economics or to mitigate environmental concerns, a recycle stream may be used to augment the initial feed or added at any intermediate point, such as between any two reactors. Where this is done the combination of initial feed and recycle stream, or of reaction product and recycle stream, may be more conveniently referred to as a "process feed," as in Examples 3 and 4 hereinbelow.

EXAMPLES

Example 1 (Comparative)

This comparative example describes adiabatic reactor art that is currently used on a commercial scale. An ethyl alcohol/water feed (92 weight percent ethyl alcohol) is combined with diluent water to form a steam-to-alcohol ratio of 3:1 by weight. The feed is then heated via a furnace to 465-470° C. and fed to an adiabatic reactor. The effluent (first reaction product) is then reheated in a furnace to 465-470° C. and fed to a second adiabatic reactor in series. The pressure at the reactor inlet is measured as 1.14 MPa, while the reactor outlet pressure is found to be 1.05 MPa. Overall catalyst liquid hourly space velocity (LHSV) of 0.5 (on a water-free basis) is used.

Overall conversion of ethyl alcohol is determined to be 99.9 mole percent, and overall selectivity to ethene is 99.4 mole percent. The overall volume of gas through the reactor system is approximately six times the volume of gas of the original ethyl alcohol/water feed. In addition, significant energy and capital expense is required to process the diluent water. This cost would be anticipated to become higher at greater scale of operation.

Example 2

An ethyl alcohol/water feed (92 weight percent ethyl alcohol) is heated in a furnace and fed to an initial adiabatic reactor containing alumina catalyst at 300° C. and at 0.3 MPa pressure absolute. This generates a first reaction product containing unreacted ethyl alcohol, water (both generated and diluent), diethyl ether, and some ethene. The first reaction product exits the first reactor at a temperature close to the temperature at which it entered the first reactor. The mass fraction of water is increased from 8 weight percent, in the initial feed, to greater than 20 weight percent in the first reaction product. This first reaction product is then fed to three subsequent adiabatic reactors operating in series, each at reactor inlet temperatures of 450° C. and at pressures ranging from 0.1 and 0.2 MPa absolute. Total LHSV of the reactors is approximately 0.5 (on a water-free basis), resulting in a greater than 98 percent conversion of ethyl alcohol to ethene. The total vapor volume is reduced by a factor of six and the amount of total water requiring separation and post treatment is also reduced, when compared with amounts shown in Example 1 (Comparative).

Example 3

An ethyl alcohol/water feed (92 weight percent ethyl alcohol) is combined with a recycle stream to form a 25 weight percent water process feed, which is then heated to 400° C. The heated process feed is fed to an initial adiabatic reactor containing alumina catalyst. The reactor is maintained at 0.6 MPa pressure absolute. The resulting first reaction product contains ethyl alcohol, water (both generated and diluent), diethyl ether, and some ethene. The mass fraction of water in the process stream is increased from 25 weight percent to 40 weight percent due to the formation of diethyl ether and ethene, while the initial process stream is exposed to significantly reduced process temperatures (65° C. lower) when compared with Example 1 (Comparative). The first reaction product is then fed to a second and then a third adiabatic reactor operating at reactor inlet temperatures from 450° C. to 470° C., respectively, and at reactor inlet pressures of 0.5 and 0.4 MPa absolute, respectively, resulting in a second reaction product exhibiting a conversion of ethyl alcohol to ethene that is 95 percent or greater.

Example 4

An azeotropic ethyl alcohol/water feed is combined with a recycle stream to form a 50 weight percent water process feed, then heated in a reactor to 425° C. This is then fed to an initial adiabatic reactor containing alumina catalyst at 0.6 MPa pressure absolute. The resulting first reaction product contains ethyl alcohol, water (both generated and diluent), diethyl ether, and some ethene. The mass fraction of water in the first reaction product is increased from 50 weight percent to greater than 55 weight percent, while the initial reactor process feed is exposed to significantly reduced process temperatures (40° C. lower) when compared with Example 1 (Comparative). The conditions in this Example 4 allow for at least a 40° C. reduction in temperature of the initial process feed temperature. The first reaction product is then heated in a second reactor to 475° C. and fed to a second adiabatic reactor operating at 0.5 MPa pressure absolute, resulting in a second reaction product exhibiting a conversion of the initial ethyl alcohol to ethene that is 95 percent or greater.

What is claimed is:
1. A process to prepare an olefin comprising
(a) reacting a feedstream comprising a C2-C4 alcohol or a combination thereof in the presence of a first dehydration catalyst in a first adiabatic reactor comprising a first reactor inlet temperature of 200° C. to 450° C.;
(b) withdrawing a first reaction product from the first adiabatic reactor wherein the first reaction product comprises a dialkyl ether and generated water in an amount of at least 5 percent by weight, based on total weight of the first reaction product;
(c) reacting the first reaction product in a second adiabatic reactor in the presence of a second dehydration catalyst to dehydrate a portion of the dialkyl ether to form an olefin and wherein the second reactor inlet temperature is at least 10° C. higher than the first reactor inlet temperature;
(d) wherein the first dehydration catalyst and the second dehydration catalyst may be the same or different; and
wherein the feedstream optionally comprises diluent water in an amount of up to 50 percent by weight, based on the weight of the C2-C4 alcohol or the combination thereof.
2. The process of claim 1 wherein the diluent water comprises an amount ranging up to 20 weight percent, based on the weight of the C2-C4 alcohol or the combination thereof.
3. The process of claim 1 wherein the second reactor inlet temperature ranges from 250° C. to 500° C.,
the first and second reactor independently comprise a pressure in the range between 0.04 to megapascals absolute, and
the first and second reactor independently comprise a residence time in the range between 0.5 second to 1 minute.
4. The process of claim 3 wherein the second reactor inlet temperature ranges from 400° C. to 450° C.
5. The process of claim 3 wherein the pressures comprise a range between 0.1 to 1.5 megapascals absolute.
6. The process of claim 3 wherein the residence times range from 0.5 to 10 seconds.
7. The process of claim 1 wherein the first and/or second dehydration catalyst is selected from a group consisting of alumina; silica-alumina; silica; titanium oxide; hafnium oxide; zirconium oxide; tungsten oxide; zeolites; phosphoric acids supported on carbon; calcium phosphates; calcium molybdates; and combinations thereof.
8. The process of claim 1 wherein the olefin is ethene, propene, butene, or a mixture thereof.
9. The process of claim 1 wherein the dialkyl ether is diethyl ether; and the olefin is ethene.
10. The process of claim 1 further comprising
e) withdrawing a second reaction product including dialkyl ether from the second adiabatic reactor;
f) reacting the second reaction product in a third adiabatic reactor to produce a third product comprising a higher amount of the olefin than was present in the second reaction product and wherein the third reactor inlet temperature is at least 10° C. higher than the second reactor inlet temperature.

* * * * *